United States Patent
Manocha

Patent Number: 5,595,486
Date of Patent: Jan. 21, 1997

[54] METHOD AND DEVICE FOR FILLING AN ENDODONTICALLY PREPARED TOOTH

[76] Inventor: Ashok Manocha, 34 Flowerwood Dr., Chattahoochee, Fla. 32324

[21] Appl. No.: 432,505

[22] Filed: Apr. 14, 1995

[51] Int. Cl.⁶ .................................................. A61C 5/02
[52] U.S. Cl. .................................. 433/224; 433/220
[58] Field of Search .......................... 433/220, 221, 433/224, 81

[56] References Cited

U.S. PATENT DOCUMENTS

| | | | |
|---|---|---|---|
| 3,855,702 | 12/1974 | Malmin | 433/224 |
| 3,908,270 | 9/1975 | Fishman | 433/224 |
| 3,919,774 | 11/1975 | Fishman | 433/224 |
| 4,758,156 | 7/1988 | Johnson | 433/81 |
| 5,051,093 | 9/1991 | Fitzmorris | 433/234 |
| 5,085,586 | 2/1992 | Johnson | 433/234 |
| 5,118,297 | 6/1992 | Johnson | 433/234 |
| 5,149,268 | 9/1992 | Johnson | 433/234 |
| 5,161,973 | 11/1992 | Johnson | 433/211 |
| 5,171,146 | 12/1992 | Guerci | 433/81 |
| 5,215,461 | 6/1993 | Riazi | 433/224 |
| 5,232,440 | 8/1993 | Wilk | 604/49 |

*Primary Examiner*—Cary E. O'Connor
*Attorney, Agent, or Firm*—Peter Loffler

[57] ABSTRACT

A device and method for filling an endodontically prepared tooth and attaching a dental post thereon is disclosed. The device consists of a carrier. Integrally attached to the carrier is a dental post. A break point is located therebetween. A filler material surrounds the carrier and part of the post. In order to install the device, the root canal is prepared. The device is properly measured and thereafter heated. The device is inserted into the prepared root canal. Thereafter, a crown buildup onto the post is performed.

16 Claims, 2 Drawing Sheets

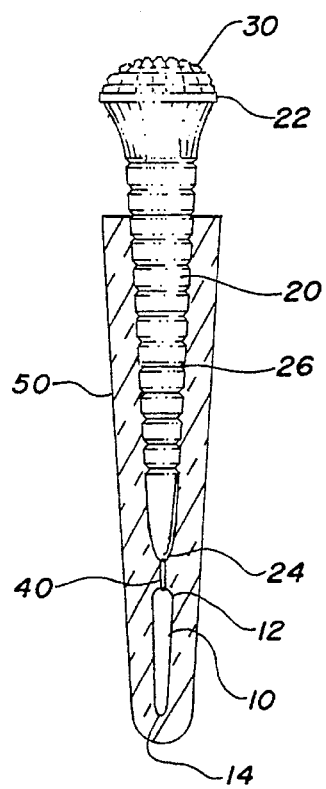
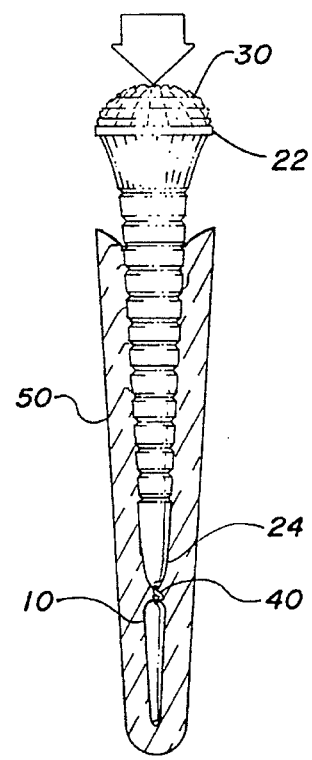
FIG. 1    FIG. 2
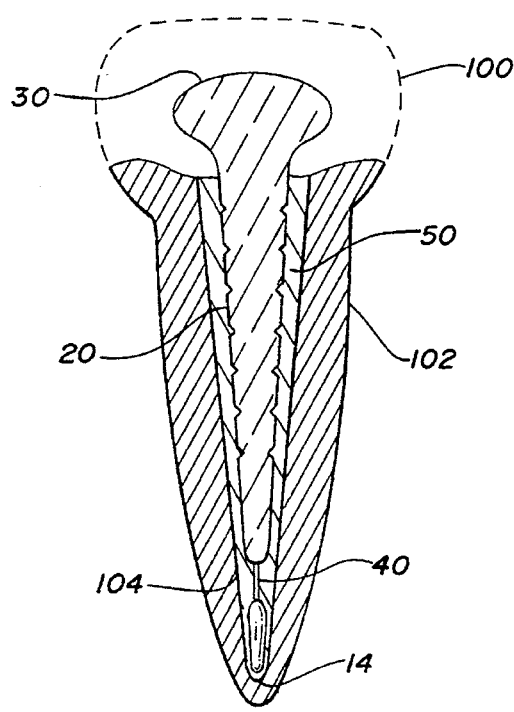
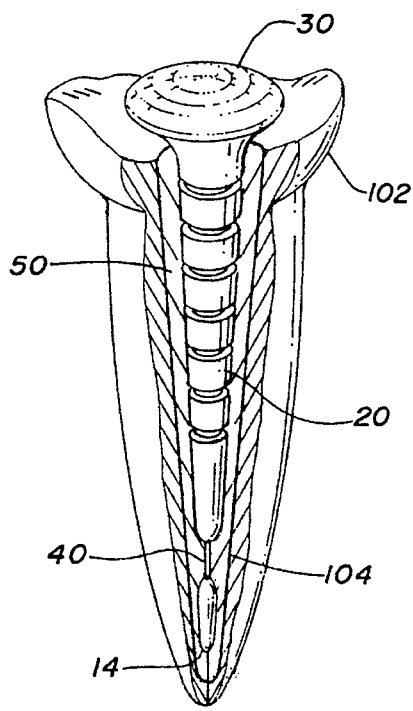
FIG. 3    FIG. 4

5,595,486

METHOD AND DEVICE FOR FILLING AN ENDODONTICALLY PREPARED TOOTH

BACKGROUND OF THE INVENTION

1. Field of the Invention

The present invention relates to an improved method and device for filling an endodontically prepared tooth and thereafter attaching a dental post thereto.

2. Background of the Prior Art

A human tooth has two parts. The root, which is located below the gum line in the bone, and the crown, which is located above the gum line. The root has within it, a canal. Located within the canal are nerves, blood vessels, and other organic tissue (pulpal).

If the canal becomes compromised, by deterioration, injury, or other causes, fluids enter the root canal causing periapical infection. These fluids cause pain and discomfort. Left unchecked these fluids will cause deterioration of the bone to the point of a required extraction.

In order to treat a compromised canal, an endodontic procedure is performed. A dentist, or more commonly an endodontic dental specialist, prepares the canal. This entails removing all nerves, blood vessels, and other tissue from the canal. The canal is then sanitized.

The canal is filled and sealed so that fluids cannot reenter the canal. The most common filling and sealing material is gutta percha.

After the procedure is completed the canal is filled and permanently sealed. The above procedure is a routine dental procedure. Efficient state of the art methods and devices are available for completion of the procedure. See for example, U.S Pat. No. 5,149,268 to Johnson.

Most patients have, in addition to a compromised canal, damage to the tooth crown. Such patients require not only an endodontic procedure as described above, but also a crown restoration.

In many cases a crown restoration entails the installation of a dental post into the root canal. Once installed, an artificial tooth crown is built up upon the dental post.

This restoration is accomplished in three steps. Step one is the endodontic preparation of the root canal by an endodontist or general dentist. Step two entails the installation of the dental post into the root canal. Finally, step three is the crown build up. The second and third steps are typically performed by a general dental practitioner.

The problem with this three step procedure is that in installing the dental post, the previously sealed root canal must be partially redrilled in order to provide a borehole to receive the dental post.

This redrilling can cause undesired results. The redrilling can break or shatter the tooth or can cause perforation of root. If this happens, the entire tooth must be removed.

What is needed is a device and method whereby steps one and two are performed simultaneously. By performing the endodontic procedure and dental post installation in one step, the second redrilling of the root canal is avoided. This results in a safer and more effective procedure for the patient.

SUMMARY OF THE INVENTION

The present invention provides a method and device so that endodontic preparation and dental post installation can be combined into one step eliminating the need to redrill a root in order to install a post.

The present invention comprises a carrier. Attached to the carrier is a dental post. A thin connector is located between the carrier and the post. The thin connector defines a break point. Gutta percha, or other similar filler material, surrounds the carrier and the lower part of the dental post.

In order to install the device, the root canal must be properly prepared. This entails properly boring the root canal and removing all nerves, blood vessels, and other tissue from the canal. The canal is then sanitized.

A proper working length for the device is obtained. The device is heated for increased viscosity of the filler material. The device is inserted into the canal. The filler material fills the voids within the root and seals the carrier and post in position.

The dental post is securely positioned within the root. The top end of the post extends 2–5 millimeters above the tooth line. This permits a crown buildup onto the post. Alternate embodiments of the post top are disclosed. These alternate embodiments increase the surface area that is in contact between the post and the crown or other dental appliance that is eventually installed on the post.

The post has horizontally disposed grooves to permit proper seating of the device within a tooth's canal. The post also has vertically disposed grooves to permit escape of any trapped air bubbles within the tooth's canal.

BRIEF DESCRIPTION OF THE DRAWINGS

FIG. 1 is a partial cutaway view of the device of the present invention.

FIG. 2 is a partial cutaway view of the device of the present invention with the break point triggered.

FIG. 3 is a cutaway view of the device of present invention installed within a tooth's canal.

FIG. 4 is a partial cutaway view of the device of the present invention.

Similar reference numerals refer to similar parts throughout the several views of the drawings.

DETAILED DESCRIPTION OF THE PREFERRED EMBODIMENT

Figure 5:
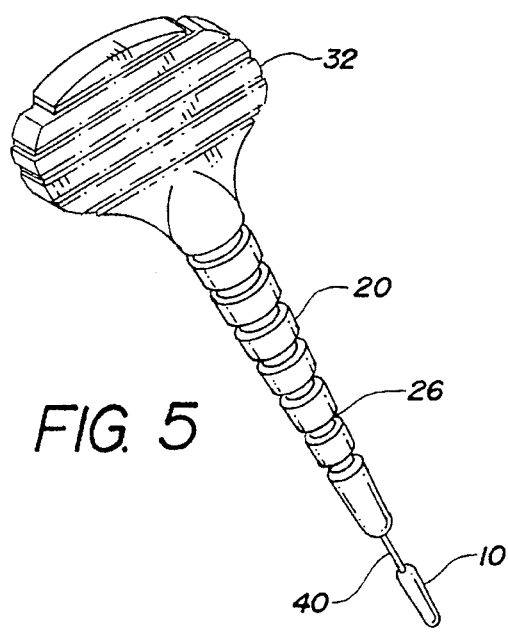
FIG. 5 is a partial perspective view of the device of the present invention.

The present invention is an improved root canal filler to be used on patients who require, in addition to a root canal procedure, a dental post or similar appliance insertion in order to build up a broken or otherwise compromised tooth. The device is designed to eliminate the need to redrill the tooth after a root canal procedure is performed in order to install a post within the tooth. A method for installing the present invention into the root canal of a patient is also disclosed.

The device of the present invention includes a carrier 10. The carrier 10 has a top end 12 and a bottom end 14. The carrier 10 can be constructed from plastic, stainless steel, titanium, or other suitable material that is bioacceptable within the canal of a tooth's root.

Located a short distance within and above the carrier 10 is a dental post 20. This post 20 is used for the buildup of the broken tooth. The post 20 has a top end 22 and a bottom end 24. The post 20 is constructed of stainless steel, titanium, or other similar bioacceptable device. The post 20 will receive a crown buildup 100 or other dental appliance once the post 20 is properly positioned within the tooth 102.

As seen, the post 20 has horizontally disposed grooves 26. These horizontally disposed grooves 26 help assure proper seating of the post 20 within the tooth's canal 104. Furthermore, the post 20 has vertically disposed grooves 28. These grooves permit air bubbles trapped within the root, to migrate out to the top of the root.

The top end 22 of the post 20 can have a bulbed end 30. This bulbed end 30 will increase the surface area of the post that is in contact with the crown 100. This will insure a more secure attachment of the crown 100 to the post 20.

Figure 6:
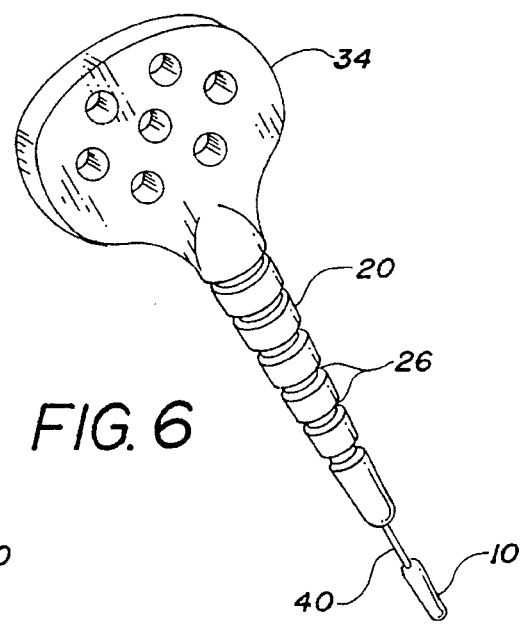
FIG. 6 is a partial perspective view of an alternate embodiment of the device of the present invention.
Figure 7:
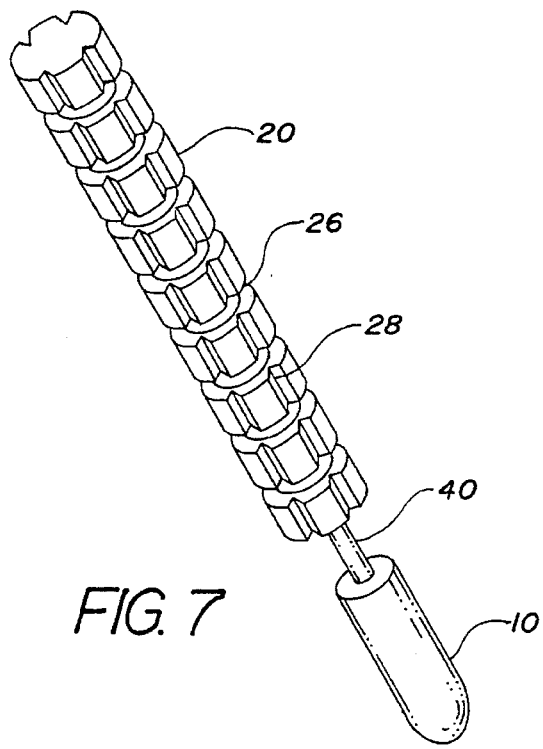
FIG. 7 is a partial perspective view of another alternate embodiment of the device of the present invention.

Alternatively, the top end 22 of the post 20 can have a spatula-type end. This spatula-type end is an alternative method by which to increase the surface area of the post 20 that is in contact with the crown 100. The spatula-type end can either be a grooved spatula 32, as seen in FIG. 5, or a perforated spatula 34, as seen in FIG. 6.

The carrier 10 is connected to the post 20 by a thin connector 40. The thin connector 40 is made of the same material as is the carrier 10 and can be integral with the carrier 10. This thin connector 40 defines a break point. The thin connector 40, by being smaller in diameter than the carrier 40, will break and thereby sever the connection between the post 20 and carrier 10, should undue pressure be applied to the post 20.

If excessive pressure is applied to a crown 100 after completion of the buildup and crown procedure, that excessive pressure is transferred to the post 20 within the root. The post will in turn, transfer the pressure to the carrier 10 that is located within the root. By being in contact with the root, the carrier 10 would transfer the pressure to the root. This pressure, if sufficient, would result in root breakage.

The thin connector 40 will break if undue pressure is applied to it. Therefore, any pressure that is placed upon the tooth's crown and transferred to the post 20, will result in thin connector breakage. As the thin connector 40 breaks, it ceases to mechanically communicate with the carrier 10. This communication severance blocks the transfer of pressure to the tooth's root, through the carrier, 10 thereby assuring the safety of the root.

No adverse consequences result from the breakage of the thin connector 40. Aside from acting as a pressure circuit breaker, the thin connector's main function is to hold the carrier 10 to the post 20, in proper alignment, before installation into a patient's tooth. Upon installation, the thin connector's structural function is complete and its sole remaining function is that of blocking pressure from reaching a root's tip.

A binder or filler such as gutta percha 50 surrounds the carrier 10 as well as the lower part of the post 20. Upon installation of the device within a patient's tooth, the binder will flow and fill the lateral recesses within a tooth's root, thereby sealing the root from outside contamination.

To install the present invention, an endodontic preparation, or "root canal," must first be performed.

In order to properly perform an endodontic procedure, the practitioner, either endodontist or dentist must remove pulpal and other contaminants from the root canal of the tooth. This is accomplished by the insertion of small diameter files into the root canal and twisting. As these files have a rough exterior surface, they will loosen the pulpal material. Through repeated twisting, the pulpal is all removed.

After the root canal is cleaned as practically as possible, it must be sealed and filled so that contaminants and body fluids cannot enter the root canal. Proper sealing of the root canal is essential to the endodontic procedure.

Sealers, such as ThermaSeal, AH-26, Sealapex, Roth's, and Kerr's Pulp Canal Sealer are all acceptable for this procedure. Immediately after the sealer is applied, the root canal must be filled. The sealer provides the needed lubrication for installation of the device.

The canal is measured for working length. The working length is that distance wherein the obturator terminates at the apical constriction of the canal (the apex), and the post extends 2–5 mm above the tooth's surface depending on the tooth. X-rays from two different angles can be used as an aid in measuring this working length. Other standard techniques, such as radiographic, electronic apex locator, pre-curved instruments, etc., can also be used.

A obturator that corresponds to the working length is selected. The device must also be chosen so that once properly seated within the root canal, there is minimal distance between the post and the patient's tooth. This tolerance must be kept to less than a millimeter to prevent post-surgical movement of the post, which would result in tooth breakage.

The obturator is disinfected preferably in a solution of 2.5%–5.25% sodium hypochloride in water, rinsed in 70% alcohol, and allowed to dry. Ambient air drying of the obturator is acceptable.

The obturator is heated by an appropriate means, such as an open flame or a specially constructed heating oven, so that the filler becomes soft. After being properly heated, the obturator is inserted into the prepared root canal. The soft filler fills the lateral voids within the canal.

In inserting the obturator, small air pockets can sometimes form with the tooth's canal. By being heated, the gutta percha attains enough viscosity to permit the air bubbles to travel through the gutta percha. The vertical grooves 28 of the post 20 permit the air bubbles to rise to the top of the canal and escape.

In handling the device of the present invention, a clamp or other handling means is employed. The device is pushed down into the prepared canal until the filler reaches the apex of the tooth's root. The device must not be pushed beyond the apex, as root breakage may result. Tactile response, coupled with precise working length determination, as described earlier, determine the stopping point in pushing the device down into the root canal. The obturator should seat into place and should not be forced into place.

After completion of the procedure, the post will be properly and permanently seated within the tooth. 2 to 5 millimeters of the post will be visible above the top of the tooth. The dental professional will be able to perform a dental buildup procedure and crown installation using appropriate standard techniques upon the post 20.

While the invention has been particularly shown and described with reference to embodiments thereof, it will be understood by those skilled in the art that various changes in form and detail may be made without departing from the spirit and scope of the invention.

I claim:

1. A obturator and post for filling an endodontically prepared root canal comprising:
   a) a post dimensioned to terminate about 2 to about 5 millimeters above the tooth;
   b) a carrier;

c) a connector, of a diameter less than the diameter of the post and the diameter of the carrier, connecting the end of the carrier to end of the post; and d) a filler that is bioacceptable within the root surrounding the carrier, the connector, and the lower part of the post.

2. The device as in claim 1 wherein the post has a plurality of circumferential grooves.

3. The device as in claim 2 wherein the post has a plurality of vertical grooves disposed perpendicularly to the circumferential grooves.

4. The device as in claim 1 wherein the post has a bulbed end opposite the end connected to the connector.

5. The device as in claim 1 wherein the post has a spatulated end opposite the end connected to the connector.

6. The device as in claim 5 wherein the spatulated end is perforated.

7. The device as in claim 5 wherein the spatulated end is grooved.

8. The device as in claim 1 wherein said filler is gutta percha.

9. The device as in claim 1 wherein said carrier is made from material selected from the group comprising plastic, steel, and titanium.

10. The device as in claim 1 where said post is made from material selected from the group comprising steel and titanium.

11. A obturator and post for filling an endodontically prepared root canal comprising:

a) a post dimensioned to terminate about 2 to about 5 millimeters above the tooth having a plurality of circumferential grooves, made from material selected from the group comprising steel and titanium;

b) a carrier made from bioacceptable material selected from the group comprising plastic, steel, and titanium;

c) a connector, of a diameter less than the diameter of the post and the diameter of the carrier, connecting the end of the carrier to end of the post; and d) gutta percha surrounding the carrier, the connector, and the lower part of the post.

12. The device as in claim 11 wherein the post has a plurality of vertical grooves disposed perpendicularly to the circumferential grooves.

13. The device as in claim 11 wherein the post has a bulbed end opposite the end connected to the connector.

14. The device as in claim 11 wherein the post has a spatulated end opposite the end connected to the connector wherein the spatulated end is perforated.

15. The device as in claim 11 wherein the post has a spatulated end opposite the end connected to the connector wherein the spatulated end is grooved.

16. A method for filling an endodontically prepared root of a tooth employing an obturator and post combination in the form a post, a carrier, a connector, of a diameter less than the diameter of the post and the diameter of the carrier, connecting the end of the carrier to end of the post, and filler that is bioacceptable within the root surrounding the carrier, the connector, and the lower part of the post comprising the steps of:

a) measuring the working length of the root's canal;

b) selecting an obturator and post combination corresponding in length to the working length;

c) heating the filler material to increase the viscosity;

d) inserting the obturator and post combination into the canal until the post extends from 2 to 5 millimeters above the upper surface of the tooth.

* * * * *